United States Patent [19]

Hopkins

[11] Patent Number: 4,795,709

[45] Date of Patent: Jan. 3, 1989

[54] SOLVENT-INDUCED AUTOLYSIS OF CELLS

[75] Inventor: Thomas R. Hopkins, Bartlesville, Okla.

[73] Assignee: Phillips Petroleum Company, Bartlesville, Okla.

[21] Appl. No.: 742,836

[22] Filed: Jun. 10, 1985

[51] Int. Cl.$^4$ .......................... C12N 1/06; C12N 9/02
[52] U.S. Cl. ..................... 435/259; 435/189; 435/938; 435/255
[58] Field of Search ............... 530/824, 426; 435/171, 435/243, 259, 255, 272, 804, 938, 247, 189

[56] References Cited

U.S. PATENT DOCUMENTS

| | | | |
|---|---|---|---|
| 785,733 | 3/1905 | Hess | 435/255 |
| 785,734 | 3/1905 | Hess | 435/255 |
| 2,536,171 | 1/1951 | Hall et al. | 435/69 |
| 3,034,900 | 5/1962 | Maranca | 99/105 |
| 3,716,462 | 2/1973 | Kitamura et al. | 204/38.4 |
| 3,737,377 | 6/1973 | Sternberg | 435/207 |
| 3,801,461 | 4/1974 | Miyake et al. | 435/193 |
| 4,144,130 | 3/1979 | Kula et al. | 435/183 |
| 4,329,429 | 5/1982 | Fenton | 435/207 |
| 4,340,675 | 7/1982 | Johansen | 435/189 |
| 4,414,334 | 11/1983 | Hitzman | 435/262 |
| 4,430,427 | 2/1984 | Hopkins | 435/25 |
| 4,450,153 | 5/1984 | Hopkins | 424/94 |
| 4,464,295 | 8/1984 | Bhaduri et al. | 424/92 |
| 4,497,730 | 2/1985 | Ames et al. | 435/879 |

FOREIGN PATENT DOCUMENTS 137995 12/1902 Fed. Rep. of Germany.

*Primary Examiner*—Charles F. Warren
*Assistant Examiner*—Irene Marx
*Attorney, Agent, or Firm*—Williams, Phillips & Umphlett

[57] ABSTRACT

A process to recover proteins, such as enzymes, from yeast cells, which comprises forming an admixture of yeast cells, water, and a minor effective amount of a polychloro aliphatic hydrocarbon, at a suitable pH, and incubating for a suitable time and temperature, such as at room temperature, of about 16 to 90 hours. The resulting supernatant is separated as an aqueous liquid containing a high enzyme activity. Enzymes can be recovered, if desired. Typical applications include *Kluyveromyces fragilis* for lactase, *Pichia pastoris* for alcohol oxidase. Typical solvents include methylene dichloride, 1,1,1-trichloroethane, and chloroform.

4 Claims, No Drawings

SOLVENT-INDUCED AUTOLYSIS OF CELLS

FIELD OF THE INVENTION

The invention pertains to a method for extraction of proteins from yeast cells. In another aspect, the invention pertains to methods to rupture cells to release proteins such as enzymes. In a further aspect, the invention pertains to methods to obtain enzymes contained in yeast cells.

BACKGROUND OF THE INVENTION

Combinations of fermentation techniques and various carbon energy substrates, and particular microorganism strains can produce valuable intracellular enzymes. It is highly desirable to break the cells and obtain the proteins contained therein, particularly the valuable enzymes, without destroying the enzymes.

A variety of approaches have been employed for the disruption of yeast cells in order to release the contained proteins, particularly enzymes. Mechanical disruption techniques have included ball milling, grinding, sonication, and the like, usually with cooling to minimize protein breakdown. Mechanical disruptions, however, generally result in some degradation of the enzymes and the resultant extremely heterogeneous mixture of cell fragments can prove difficult to separate effectively from the soluble fraction. Added enzymes have been employed to effect a destruction or disruption of the cell walls and release of the cellular contents. However, added enzymes can be expensive and introduce foreign proteins and may pose undesired separatory problems, or cause desired side effects in uses of the desired enzymes.

Chemical methods have been employed to cause autolysis (plasmolysis), including various hydrocarbons such as toluene; carbonyl compounds including ethyl acetate, acetone, other dialkyl ketones; and other chemicals such as ethyl ether and alcohols such as $C_1$ to $C_4$ alkanols. These chemical approaches have had varying results depending upon the organism, its growth conditions, and the time of exposure to and concentration of the solvent. Some have been hazardous since at desired treatment temperatures volatility may produce flammable, indeed, explosive conditions. Some require high concentrations of lytic solvents which may lead to separation problems in subsequent purification steps.

Needed, still, are new treatments to produce good results in protein release from cells, yet employing safe materials, mild conditions and a minimum of added lytic component.

BRIEF SUMMARY OF THE INVENTION

I have discovered that relatively quite low concentrations of certain polychloro aliphatic treating agents in water, combined with an incubation of some hours at about room temperature, results in lysis (breakage) of the yeast cells and release of the intracellular products including enzymes and other proteins.

My method employs very small amounts of polychloro aliphatic treating agents in water in admixture with the yeast cells as an aqueous dispersion, and the resulting ter-mixture is allowed to incubate for a desired time. This method results in substantially all of the cells being suitably broken, generally at least about 80 number percent of the cells, releasing the soluble protein contents into the aqueous dispersion, where the enzymes and other proteins then can be recovered by usual procedures.

My method employing polychloro aliphatic treating agents to produce solvent-induced autolysis is mild, reliable, efficient, results in good enzyme recovery and is not labor intensive. Very small amounts of polychloro aliphatic treating agents are involved, which do not interfere in recovery procedures, and need not be separated. They can, indeed, serve as a bacteriostatic agent during any desired purification steps to follow the cell lysis.

POLYCHLORO COMPOUNDS

The polychloro aliphatic treating agents I employ can be termed polychloro derivatives of non-benzenoid hydrocarbons. More particularly, these are polychloro derivatives of alkanes, and are normally liquid at standard temperature and pressure.

Among the polychloro derivatives of alkanes which can be employed, and which compounds ar liquid at normal temperature and pressure, are the following examples which can be used alone or in admixture, and which are intended to be illustrative and not limitative:

methylene chloride,
1,2 dichloroethylene (cis or trans),
ethylidene chloride,
chloroform,
2,2-dichloropropane,
1,1,1-trichloroethane,
carbon tetrachloride,
ethylene chloride,
trichloroethylene,
propylene chloride,
1,1,2-trichloroethane,
tetrachloroethylene,
trimethylene chloride,
s-tetrachloroethane,
1,2,3-trichloropropane, and
pentachloroethane.

Presently preferred as chloroform or methylene chloride.

SCOPE OF YEASTS

According to my procedure, I employ yeast cells grown on carbon-containing substrates under aqueous, aerobic fermentation conditions.

Suitable yeasts include species from the genera such as Candida, Hansenula, Torulopsis, Saccharomyces, Pichia, Debaryomyces, and Brettanomyces. The presently preferred genera include Candida, Hansenula, Torulopsis, Pichia, Kluyveromyces, and Saccharomyces. Examples of suitable species include:

*Brettanomyces petrophilium,*
*Candida boidinii,*
*Candida lipolytica,*
*Candida mycoderma,*
*Candida utilis,*
*Candida stellatoides,*
*Candida robusta,*
*Candida claussenii,*
*Candida rugosa,*
*Candida tropicalis,*
*Debaryomyces hansenii,*
*Hansenula minuta,*
*Hansenula saturnus,*

*Hansenula californica,*
*Hansenula silvicola,*
*Hansenula polymorpha,*
*Hansenula wickerhamii,*
*Hansenula capsulata,*
*Hansenula glucozyma,*
*Hansenula henricii,*
*Hansenula nonfermentans,*
*Hansenula philodenra,*
*Hansenula holstii,*
*Pichia farinosa,*
*Pichia polymorpha,*
*Pichia membranefaciens,*
*Pichia pinus,*
*Pichia pastoris,*
*Pichia trehalophila,*
*Saccharomyces cerevisiae,*
*Saccharomyces fragilis,*
*Saccharomyces rosei,*
*Saccharomyces acidifaciens,*
*Saccharomyces elegans,*
*Saccharomyces rouxii,*
*Saccharomyces lactis,*
*Torulopsis sonorensis,*
*Torulopsis candida,*
*Torulopsis bolmii,*
*Torulopsis versatilis,*
*Torulopsis glabrata,*
*Torulopsis molishiana,*
*Torulopsis nemodendra,*
*Torulopsis nitratophila,*
*Torulopsis pinus,* and
*Torulopsis bombicola.*

If desired, mixtures of two or more species of yeasts can be employed. The particular yeast(s) employed depends in part on the carbon-containing substrate to be used since it is well known that different yeasts often require somewhat different substrates for best growth; or, that specific biochemical conversions are best conducted by specific yeast genera or species. For example, it is recognized that some particular strains of species listed above do not grow well on methanol, i.e., do not utilize methanol.

METHOD OF TREATMENT

The yeast cells conveniently are treated as a cellular cream containing a substantial concentration of whole yeast cells, such as a solids content of about 8.5 to 15, preferably 10 to 13, weight percent (dry basis) based on the whole cells. The yeast cells can be admixed with water and my polychloro-treating component to form a slurry which should contain about 85 to 150, preferably about 100 to 130, grams of cells per liter. Lower cell concentrations can be employed, though results may not be as satisfactory. Present data indicate that at cell concentrations as low as 2 to 3 weight percent that enzyme release does not occur.

The remaining percentage of the aqueous cream or cellular slurry is essentially water, and the polychloro-treating agent. The water component can be pure water, water containing dilute salts or the natural liquor of the fermentor effluent as may be convenient, available, or desired.

Based on the total of the three-component system, the amount of polychloro-treating agent should be that effective to achieve autolysis of the particular cells with the agent chosen and the time and temperature employed. Suggested is a range of about 0.8 to 6, preferably about 1.5 to 4 volume percent.

Admixing can be by any convenient manner, such as pouring together, stirring, and the like, depending on the quantities and materials to be employed. There is no need for physical beating or violent admixing as to cause physical rupture of cells.

Any order of admixing is suitable; cells with water components, and then adding my polychloro-treating compound, presently is preferred. However, the polychloro compound and water component can be admixed first, and the yeast cells then added thereto.

Preferred and convenient is the employment of the aqueous ferment itself exiting the fermentation step and which contains both supernatent aqueous liquor and suspended yeast cells. If desired, the cells can be separated by such as centrifugation or filtering, water-washed if desired for removal of residual mineral matter, and resuspended in fresh water. Alternatively, the cellular concentration in an aqueous ferment can be increased, if needed, by such as filtration, centrifugation, solvent removal, or the like. If the aqueous ferment is from a high cellular density yeast fermentation process, such aqueous ferment can be used as is, if desired.

pH

The three-component system should be initially adjusted as to pH preferably to a pH of at least about 7, though such as about 6.5 to 8.5 is suitable, and preferably to about 7.25 to 8 initial pH adjustment, the pH of some aqueous yeast dispersions tend to decrease slightly with time. The pH of aqueous ferments for production of yeast cells usually are somewhat on the acidic side. In some instances, addition of small amounts of dilute ammonium hydroxide or sodium hydroxide, or similar alkali, preferably in a dilute solution, can be employed to adjust the pH.

TEMPERATURE

The temperature of contacting can be as convenient, such as substantially room temperature, or the temperature of the aqueous ferment as it normally comes from the fermentor when the aqueous ferment itself is to be directly employed.

Usually, a contacting temperature of about 20° to 35° C., more preferably about 25° to 35° C., is employed.

Conveniently, and preferably, the contacting temperature is that employed for holding or incubation.

HOLDING TIME

The "holding" time or "incubation" time should be a time of at least about 16 hours, more usually about 16 to 90 hours, presently preferably about 24 to 48 hours.

The three-component system, yeast cells, water, and polychloro-treating compound, in admixture, can be maintained in a suitable hold vessel or tank which can be stainless steel, glass-lined, or similar, for the desired time. The fermentation vessel itself can be used as the holding vessel. The pH and temperature should be maintained as described above. Normally, continuous stirring is not required, though a mild stirring or admixture can be employed, if desired.

There is no present known necessity to shield the contents from air or oxygen, though usually a closed container is suggested to minimize loss of the polychlorohydrocarbon solvent from the vessel.

There is no present known necessity to shield the contents from light, though normally the holding vessel is in darkness.

During this holding or incubation time, the cell walls of the yeast cells break, rupture, disintegrate, and otherwise release their proteinaceous contents to the aqueous environment.

Thereafter, the proteins including enzymes can be recovered.

RECOVERY

A variety of approaches have been employed for the recovery of contained proteins, especially enzymes, from the lysated cells. The resulting protein-containing aqueous liquor from my treating process step can be centrifuged, if desired, for removal of cell debris and other suspended solids. The soluble proteins in the protein-containing aqueous liquor can be recovered from the solids phase by solvent partition, adsorption on a solid matrix ultrafiltration, centrifugation, and precipitation, or by a combination of such processes. The preferred recovery method in my procedure is centrifugation and/or ultrafiltration, especially for the recovery of such as alcohol oxidase and lactase enzymes.

ENZYMES

The invention is particularly applicable to the recovery of enzymes from microorganisms which are highly productive in particular enzymes. For example, *Kluyveromyces fragilis* is highly productive of lactase. *Pichia pastoris*, at least certain strains particularly when grown on methanol as substrate, produces large quantities of highly desirable alcohol oxidase, as well as such as catalase, formate dehydrogenase, and the like.

EXAMPLES

Examples provided are intended to assist one skilled in the art to a further understanding of my invention. Particular materials employed should be considered as exemplary and not limitative. The specification including text, examples, data, and claims, should be viewed as a whole in considering the reasonable and proper scope of my invention.

FERMENTATION DESCRIPTION

The following fermentation description is typical of several fermentations carried out to provide cell-containing effluent for further treatment as described in the following examples.

In a continuous aerobic fermentation process, methanol and an aqueous mineral salts medium in a volume ratio of about 40 to 60, respectively, were fed individually to a fermentor, inoculated with the yeast species *Pichia pastoris* NRRL Y-11430, at a rate such that methanol was the growth-limiting factor. The fermentor was a 1500-liter foam-filled fermentor with a liquid volume of about 610 liters, with automatic pH, temperature, and level control. Agitation was provided by two conventional paddle-type turbines driven at 1000 rpm. The aeration rate was about 4 volumes of air (at about 38 psig and about 25° C.) per volume of ferment in the fermentor per minute. Anhydrous ammonia was added at a rate sufficient to maintain a pH of about 3.5 in the fermentation mixture.

The aqueous mineral salts medium was prepared by mixing, with each liter of tap water, 15.86 mL 75 wt. percent $H_3PO_4$, 9.53 g $K_2SO_4$, 7.8 g $MgSO_4.7H_2O$, 0.6 g $CaCl_2.2H_2O$, and 2.6 g 85 wt. percent KOH. The aqueous mineral salts medium was fed at a rate of 31.5 liters per hour and the methanol at a rate of 21 liters per hour.

The trace mineral solution was prepared by mixing, for each liter of solution 65 g $FeSO_4.7H_2O$, 20 g $ZnSO_4.7H_2O$, 3.0 g $MnSO_4.H_2O$, 6.0 g $CuSO_4.5H_2O$, 5.0 mL conc. $H_2SO_4$, and sufficient deionized water to make 1 liter of solution. The trace mineral solution plus biotin was prepared by mixing 780 mL of a trace mineral solution, 20 mL water, 200 mL methanol and 0.032 g biotin. The trace mineral solution plus biotin was fed separately via the methanol stream at a rate of 10 mL per liter of methanol.

The fermentation was conducted at about 30° C. and about 38 psi pressure, with an average retention time of about 11.6 hours. The cell density typically was about 128.4 g of cells per liter of fermentor effluent. The total solids content of the ferment typically was about 134.7 g per liter.

The resulting yeast cells were separated from the fermentation effluent (aqueous ferment) by centrifugation, washed by suspension in water, followed by recentrifugation, dried overnight at 100° C., and weighed. On a dried basis, the yield of yeast cells typically was about 40.6 g per 100 g of methanol fed.

EXAMPLE I

To an aqueous cream or slurry of *Pichia pastoris* NRRL Y-11430 containing about 130 grams whole cells per liter, obtained from a high cellular density fermentation employing methanol as substrate substantially as described above in Fermentation Description was added sufficient dilute sodium hydroxide to adjust the pH to about 7.5.

To 15 mL increments of the pH-adjusted slurry was added 0.5 mL of selected treating agent. The resulting treating admixtures were kept at room temperature for about two days with occasional mixing. Each sample then was centrifuged, and an assay made of the supernatant for alcohol oxidase activity. The following results were obtained:

TABLE I

| Run | Solvent Employed | Resulting Activity Alcohol Oxidase[a] |
|---|---|---|
| 1 | water | none |
| 2 | 0.5 g sodium acetate | negligible |
| 3 | tetrahydrofuran | negligible |
| 4 | hexane | negligible |
| 5 | chloroform | 63.9 |
| 6 | toluene | 6.4 |
| 7 | diethyl ether | 0.33 |
| 8 | diethyl ether (0.1 mL) | negligible |
| 9 | 0.6% sodium azide | negligible |
| 10 | dimethyl sulfoxide | negligible |
| 11 | acetone | negligible |
| 12 | 1% Triton X-100[b] | negligible |
| 13 | ethylacetate | negligible |

[a]Enzyme Units/mL as measured by an o-dianisidine/peroxidase method.
[b]Rohm-Haas surfactant.

Hexane and diethyl ether are known treating agents and used for comparison. It is evident that Run 5 of my invention is by order of some magnitude superior at the concentration employed.

EXAMPLE II

To 50 mL samples of *Pichia pastoris* aqueous slurry prepared substantially similarly as described above with pH adjusted, were added 1.5 mL of selected treating agents, mixed, and left at room temperature. After 24 hours, an additional 1.5 mL of treating agent was added to the hexane sample. Run 17 below prepared with 3 mL of diethyl ether had a total incubation time of about 48 hours. The other samples also had total incubation times of 48 hours. Samples were centrifuged and assayed as described above.

TABLE II

| Run | Treating Agent | Total Amount of Treating Agent | Resulting Alcohol Oxidase Activity of Supernatant[a] |
|---|---|---|---|
| 14 | Hexane | 3.0 ml | 0.47 |
| 15 | Chloroform | 1.5 ml | 189.7 |
| 16 | Diethyl ether | 1.5 ml | 0 |
| 17 | Diethyl ether | 3.0 ml | 219.6 |
| 18 | Toluene | 1.5 ml | 48.5 |

[a]See footnote (a) in Table I.

At the high concentration, diethyl ether produced a supernatant showing substantial alcohol oxidase activity. However, this prior art method is subject to the use of a highly flammable potentially explosive material. My inventive run with chloroform shows very high activity similar to that produced by diethyl ether, yet employing a relatively safe reagent at lower concentration. It was also noted that these treated cell mixtures can be sedimented by centrifugation at lower g-force than physically disrupted cells (bead mill or french press) and yield a very clear supernatant.

Runs with hexane and toluene were substantially ineffective.

EXAMPLE III

*Pichia pastoris* NRRL Y-11430 again was produced substantially as described hereinabove. The *Pichia pastoris* aqueous slurry contained about 130 grams cells per liter, contained about 0.01 weight percent sodium azide, and was adjusted to pH 7.5 as described before. Various amounts of chloroform or methylene chloride were added, and the resulting admixtures were left at room temperature for about four days (96 hours) with occasional shaking. Each sample then was centrifuged at 13,000 rpm for 15 minutes, and the supernatant stored at 4° C. and analyzed thereafter for alcohol oxidase about two days later.

TABLE III

| Run No. | Treating Agent | mL of Treating Agent for 50 mL of Pichia slurry | Alcohol Oxidase Assay[a] | Color of Solution |
|---|---|---|---|---|
| 19 | Chloroform | 0.5 | 366.8 | Deep red |
| 20 | Chloroform | 1.0 | 318.5 | Red |
| 21 | Chloroform | 1.5 | 235.7 | Red |
| 22 | Methylene chloride | 0.5 | 311.6 | Deep red |
| 23 | Methylene chloride | 1.0 | 149.5 | Red |
| 24 | Methylene chloride | 1.5 | 209.3 | Red |

[a]See footnote (a) in Table I.

Results above show that both chloroform and methylene chloride produce highly desirable supernatants containing alcohol oxidase. It appears that the smaller amounts of the polychlorocarbon are most productive for the relatively long incubation time employed.

EXAMPLE IV

Further runs were made employing again the *Pichia pastoris* as described hereinabove, employing substantially the same procedures. However, a 48-hour incubation was employed rather than the 96 hour of the previous Example. The resulting supernatants were maintained at about 4° C. for two days prior to assay. Amounts of *Pichia pastoris* employed again were a 50 mL volume in each instance, containing about 130 grams cell per liter. Results were as shown in Table IV:

TABLE IVA

| Run No. | Treating Agent | mL of Treating Agent for 50 mL of Pichia Slurry | Alcohol Oxidase Assay[a] | Color of Solution |
|---|---|---|---|---|
| 25 | Chloroform | 0.5 mL | 147 | Bright orange |
| 26 | Methylene chloride | 0.5 mL | 149 | Bright orange |
| 27 | Methylene chloride | 0.2 mL | negligible | Bright orange |
| 28 | 1,1,1-trichloroethane | 0.5 mL | 159 | Bright orange |

[a]See footnote (a) Table I.

Each of the polychlorinated treating agents were effective. A minimum is readily ascertainable, as shown by the Runs with the methylene chloride.

The above runs were repeated except employing a three-day incubation rather than the above two days. Results obtained were as shown in Table IVB:

TABLE IVB

| Run No. | Treating Agent | Agent for 50 mL of Pichia Slurry | Alcohol Oxidase Assay[a] |
|---|---|---|---|
| 29 | Methylene chloride | 1.0 mL | 186 |
| 30 | Methylene chloride | 0.5 mL | 72 |
| 31 | 1,1,1-trichloroethane | 0.5 mL | 298 |
| 32 | diethyl ether | 1.5 mL | 289 |
| 33 | None | — | 2 |

[a]See footnote (a) Table I.

These comparable results show high effectiveness for the trichloroethane and the methylene chloride. Comparing these results with those shown in the Table IVA above, it appears that, possibly, at the lower amounts of methylene chloride at 0.5 mL that the longer incubation time is less preferred.

EXAMPLE V

Runs were made to consider the effect of pH on solvent-induced autolysis of yeast cells. The yeast cells chosen again were the *Pichia pastoris* NRRL-Y-11430 grown on methanol as carbon energy substrate as described hereinabove. 50 mL volume portions of the *Pichia pastoris* yeast cells were adjusted with dilute ammonium hydroxide to a pH in the range from 6.5 to 8.0. Each sample contained about 130 grams cells per liter. To each sample was added 1.0 mL methylene chloride. Each sample was incubated for two days, following which each sample was centrifuged and alcohol oxidase activity determined on the supernatant. Results obtained are as follows:

TABLE V

| Run No. | pH at Start | pH after Incubation | Alcohol Oxidase Assay[a] |
|---|---|---|---|
| 34 | 6.5 | 6.2 | negligible |
| 35 | 7.0 | 6.5 | 80 |
| 36 | 7.25 | 6.6 | 124 |
| 37 | 7.5 | 6.7 | 166 |
| 38 | 7.75 | 6.9 | 139 |
| 39 | 8.0 | 7.0 | 152 |

[a]See footnote (a) Table I.

It appears from these Runs that the adjusted pH of the cell admixture preferably should be at least about 7 at the beginning of the incubation, and probably preferably about 7.5. Why the pH decreased during incubation somewhat is unknown, but possibly some slight carbon dioxide pickup from the atmosphere or acids produced by cellular metabolism may have been involved.

EXAMPLE VI

*Kluyveromyces fragilis* NRRL Y-2264 was grown under aqueous aerobic fermentation conditions employing a fermentation temperature of 37° C. and employing a crude lactase (cheese whey permeate) as carbon energy substrate. To 50 mL volume samples of the *Kluyveromyces fragilis*, each sample containing about 4.5 g (9 weight percent) yeast cells, was added sufficient dilute sodium sodium hydroxide to adjust the pH to about 7.5.

To each pH-adjusted sample was then added 0.5 mL methylene chloride or trichloroethane. The lactase activity of the supernatant was steady at intervals of 24, 28, and 96 hours of incubation. The lactase enzyme activity was determined by the beta-galactosidase method of assay.

TABLE VI

| Run No. | Treating Agent | Incubation Time | Lactase Activity[a] |
|---|---|---|---|
| 40 | Methylene chloride | 24 hours | 10.8 |
| 41 | Methylene chloride | 48 hours | 8.3 |
| 42 | Methylene chloride | 72 hours | 5.2 |
| 43 | Trichloroethane | 24 hours | 4.2 |
| 44 | Trichloroethane | 48 hours | 8.57 |
| 45 | Trichloroethane | 72 hours | 6.94 |

[a]See footnote (a) Table I.

It appears that for each solvent that there is an optimum incubation time for a given concentration of treating agent, which can be readily determined as shown above.

EXAMPLE VII

*Kluyveromyces fragilis* Y-2264 was again grown under aqueous aerobic fermentation conditions similarly as described in Example VI above, employing a pH of about 4.7, fermentation temperature 37° C., with a low vitamin content.

The aqueous slurry of the yeast cells was adjusted to a pH of 7.5 employing concentrated sodium hydroxide. To 50 mL portions of the yeast slurry, each sample containing about 110 gram cells per liter yeast cells, were added various amounts of either methylene chloride or trichloroethane. Each sample was incubated at room temperature for about 48 hours, with occasional shaking. Each sample then was centrifuged, and the supernatants were assayed for lactase activity by the beta-galactosidase method. Final pH after the incubation time was estimated to be about 7.0 for each sample. Results are as follows:

TABLE VIIA

| Run No. | Treating Agent | mL Added | Lactase Activity[a] |
|---|---|---|---|
| 46 | Methylene chloride | 0.2 | none |
| 47 | Methylene chloride | 0.5 | 7.88 |
| 48 | Methylene chloride | 1.0 | 4.88 |
| 49 | Methylene chloride | 1.5 | 3.68 |
| 50 | Trichloroethane | 0.2 | none |
| 51 | Trichloroethane | 0.5 | 4.97 |
| 52 | Trichloroethane | 1.0 | 4.11 |

TABLE VIIA-continued

| Run No. | Treating Agent | mL Added | Lactase Activity[a] |
|---|---|---|---|
| 53 | Trichloroethane | 1.5 | 7.11 |

[a]See footnote (a) Table VI.

The results show that there appears to be an optimum concentration of polychloro-treating agent for a given agent, which can vary with the particular yeast strain involved. Maximum activity is readily determinable as shown above.

Additional portions of the *Kluyveromyces fragilis*, shown as described above, were employed. The starting pH was varied, employing concentrated sodium hydroxide. To each sample was added 1 mL of treating agent to each 50 mL sample of yeast cells containing about 110 grams cells per liter. The samples were incubated at room temperature with occasional shaking for two days time. Each sample then was centrifuged, and the supernatants assayed by the beta-galactosidase assay for lactase activity. Results are as follows:

TABLE VIIB

| Run No. | Treating Agent | Initial pH | Final pH | Lactase Activity[a] |
|---|---|---|---|---|
| 54 | Methylene chloride | 6.5 | 6.43 | none |
| 55 | Methylene chloride | 7.0 | 6.72 | 4.28 |
| 56 | Methylene chloride | 7.25 | 6.75 | 4.28 |
| 57 | Methylene chloride | 7.5 | 6.84 | 4.28 |
| 58 | Methylene chloride | 7.75 | 6.88 | 4.71 |
| 59 | Methylene chloride | 8.0 | 6.96 | 4.88 |
| 60 | Trichloroethane | 6.5 | 6.23 | 4.97 |
| 61 | Trichloroethane | 7.0 | 6.40 | 7.97 |
| 62 | Trichloroethane | 7.25 | 6.45 | 7.8 |
| 63 | Trichloroethane | 7.5 | 6.49 | 8.83 |
| 64 | Trichloroethane | 7.75 | 6.49 | 8.91 |
| 65 | Trichloroethane | 8.0 | 6.50 | 7.28 |

[a]See footnote (a) Table VI.

Results show good effectiveness for my polychloro aliphatic treating agent anzyme extractive method in the pH range of about 7 to 8.

EXAMPLE VIII

The data in this example illustrates the significance of initial cell density. *Pichia pastoris* NRRL Y-11430 were grown essentially as described hereinabove. Fifty mls of yeast cell slurry were diluted with 4 volumes of *Pichia pastoris* cell media to give a cell density ≈2.5 weight percent. This (diluted) sample and an undiluted control sample were both adjusted to a pH range of 7.9–8.2, and made 1% in methylene chloride and 0.01% in sodium azide as described earlier. Both samples were incubated 22 hrs at 32°–35° C. during which period the cells in both samples settled out.

TABLE VIII

| Run No. | Color of Supernatant | (total) A.O. ≠ activity in supernatant |
|---|---|---|
| 54-control | red | 398 EU |
| 55-diluted | yellow | 40 EU |

≠ by ABTS assay method

Thus, it is observed that the lower cellular density of Run 55 of the order of 2 to 3 weight percent adversely affected the resultant A.O. activity in the supernatant, and reduced the available A.O. activity beyond the result to be expected merely from the dilution factor.

The disclosure, including data, has illustrated the value and effectiveness of my invention. The Examples, the knowledge and background of the field of the invention and the general principles of chemistry and of other applicable sciences have formed the bases from which the broad descriptions of my invention including the ranges of conditions and the generic groups of operant components have been developed, and formed the bases for my claims here appended.

I claim:

1. A process for the recovery of alcohol oxidase from whole cells of *Pichia pastoris* grown on methanol which comprises
    (a) forming an aqueous mixture of said whole cells, wherein said cells are present in an amount of from 85 to 150 grams per liter of aqueous mixture and from 0.8 to 6 volume percent of a treating agent selected from the group consisting of chloroform, 1,1,1-trichloroethane and methylene chloride or mixtures thereof, and wherein, said aqueous mixture has a pH of about 6.5 to about 8.5;
    (b) incubating said aqueous mixture at a temperature of about 20° to 35° C. for a time of about 16 to 90 hours whereby at least a portion of said alcohol oxidase is released from said cells thereby forming a alcohol oxidase-containing aqueous liquor; and
    (c) separating alcohol oxidase-containing liquor liquid from solid cell material.

2. The process of claim 1 wherein said treating agent is chloroform.

3. The process of claim 1 wherein said treating agent is 1,1,1-trichloroethane.

4. The process of claim 1 wherein said treating agent is methylene chloride.

* * * * *